United States Patent
Kao et al.

(10) Patent No.: US 8,461,347 B2
(45) Date of Patent: Jun. 11, 2013

(54) PROCESS FOR PREPARING FORM A OF ATAZANAVIR SULFATE

(75) Inventors: Ai-Hua Kao, Taitung (TW); Chia-Ying Lee, Tainan (TW)

(73) Assignee: Scinopharm Taiwan, Ltd., Tainan (TW)

( * ) Notice: Subject to any disclaimer, the term of this patent is extended or adjusted under 35 U.S.C. 154(b) by 87 days.

(21) Appl. No.: 13/204,118

(22) Filed: Aug. 5, 2011

(65) Prior Publication Data
US 2013/0035493 A1    Feb. 7, 2013

(51) Int. Cl.
C07D 213/06    (2006.01)

(52) U.S. Cl.
USPC ........................................ 546/332

(58) Field of Classification Search
None
See application file for complete search history.

(56) References Cited

U.S. PATENT DOCUMENTS

| | | |
|---|---|---|
| 5,849,911 A | 12/1998 | Fassler et al. |
| 6,087,383 A | 7/2000 | Singh et al. |
| 7,829,720 B2 | 11/2010 | Kim et al. |
| 2005/0256202 A1 | 11/2005 | Kim et al. |
| 2009/0203630 A1 | 8/2009 | Kim et al. |

FOREIGN PATENT DOCUMENTS
WO    WO/2009/136365    11/2009

OTHER PUBLICATIONS

Xu et al., Process Research and Development for an Efficient Synthesis of the HIV Protease Inhibitor BMS-232632, *Organic Process Research & Development*, 2002, 6, p. 323-328.

*Primary Examiner* — Zinna Northington Davis
(74) *Attorney, Agent, or Firm* — Enshan Hong; Kent H. Cheng; VLP Law Group LLP

(57) ABSTRACT

A process of making Form A of atazanavir sulfate comprises: a) mixing atazanavir free base with a solvent selected from the group consisting of methanol (MeOH), ethanol (EtOH), isopropanol (IPA), N-methylprrolidone (NMP) and combinations thereof; b) reacting sulfuric acid with the atazanavir free base in the mixture formed in step a) to form a reaction solution comprising atazanavir sulfate; c) mixing an antisolvent with the reaction solution; d) seeding the mixture formed in step c) with an effective amount of Form A of atazanavir sulfate to form a seeded mixture comprising Form A of atazanavir sulfate; and e) isolating Form A of atazanavir sulfate in solid form from the seeded mixture; wherein the antisolvent is selected from the group consisting of methyl tert-butyl ether (MTBE), ethyl acetate (EtOAc), acetonitrile (MeCN), isopropyl acetate (IPAc), cyclohexane, and combinations thereof. In one alternative, step c) may be performed before step b). In another alternative, step d) may be carried out concurrent with or prior to step c).

15 Claims, No Drawings

PROCESS FOR PREPARING FORM A OF ATAZANAVIR SULFATE

BACKGROUND OF THE INVENTION

1. Field of the Invention

The present application relates to process of making atazanavir sulfate, in particular process of making crystalline Form A of atazanavir sulfate.

2. Description of the Related Art

Atazanavir sulfate is an azapeptide inhibitor of HIV-1 protease. It is currently marketed under the trade name REYATAZ® and indicated in combination with other antiretroviral agents for the treatment of HIV-1 infection. The chemical name for atazanavir sulfate is (3S,8S,9S,12S)-3,12-Bis(1,1-dimethylethyl)-8hydroxy-4,11-dioxo-9-(phenylmethyl)-6-[[4-(2-pyridinyl)phenyl]methyl]-2,5,6,10,13-pentaazatetradecanedioic acid dimethyl ester, sulfate (1:1). Its molecular formula is $C_{38}H_{52}N_6O_7 \cdot H_2SO_4$, which corresponds to a molecular weight of 802.9 (sulfuric acid salt). The free base molecular weight is 704.9. Atazanavir sulfate has the following structural formula:

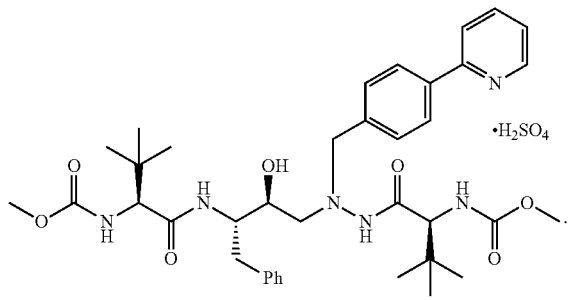

U.S. Pat. No. 6,087,383 discloses a process of making atazanavir sulfate in Form A (which is referred to as Type I crystals in Example 3 of U.S. Pat. No. 6,087,383). The process comprises dissolving atazanavir base in a mixture of acetone and 5 M sulfuric acid aqueous solution at 50° C. followed by seeding with Form A of atazanavir sulfate crystals.

U.S. Pat. No. 7,829,720 also discloses a process of making atazanavir sulfate in Form A. The process comprises dissolving atazanavir base in a mixture of concentrated sulfuric acid, acetone, and N-methylpyrrolidone (NMP). After the mixture is seeded with Form A of atazanavir sulfate crystals, the resulting atazanavir sulfate in Form A is then obtained.

The two processes respectively disclosed in U.S. Pat. Nos. 6,087,383 and 7,829,720 use acetone along with sulfuric acid to prepare atazanavir sulfate in Form A. Mesityl oxide (4-methyl-3-penten-2-one), a potential genotoxic impurity (PGI), is very likely to be formed in the processes disclosed in U.S. Pat. Nos. 6,087,383 and 7,829,720. An extremely accurate analytical method is required to monitor content of the undesired mesityl oxide impurity in a final atazanavir sulfate product.

Xu et al, Organic Process R & D 2002, 6, 323 also discloses a process of preparing atazanavir sulfate in Form A. The process comprises dissolving atazanavir base in a mixture of EtOH and concentrated sulfuric acid. The resulting mixture is treated with n-heptane to facilitate precipitation of atazanavir sulfate in Form A. n-Heptane comprises many small amounts of side products. Many residual solvent impurities are detected in final atazanavir sulfate product via head space GC.

Therefore, there is still a need for an improved process of making atazanavir sulfate in Form A.

SUMMARY OF THE INVENTION

In accordance with the present invention, a process of making Form A of atazanavir sulfate comprises:

a) mixing atazanavir free base with a solvent selected from the group consisting of methanol (MeOH), ethanol (EtOH), isopropanol (IPA), N-methylprrolidone (NMP) and combinations thereof;

b) reacting sulfuric acid with the atazanavir free base in the mixture formed in step a) to form a reaction solution comprising atazanavir sulfate;

c) mixing an antisolvent with the reaction solution;

d) seeding the mixture formed in step c) with an effective amount of Form A of atazanavir sulfate to form a seeded mixture comprising Form A of atazanavir sulfate; and e) isolating Form A of atazanavir sulfate in solid form from the seeded mixture;

wherein the antisolvent is selected from the group consisting of methyl tert-butyl ether (MTBE), ethyl acetate (EtOAc), acetonitrile (MeCN), isopropyl acetate (IPAc), cyclohexane, and combinations thereof.

In one alternative, step c) may be performed before step b). In other words, the antisolvent may be first mixed with the mixture formed in step a) before the atazanavir free base is reacted with sulfuric acid.

In another alternative, steps c) and d) may be carried out concurrently, i.e., the antisolvent and seeding material, Form A of atazanavir sulfate, may be added concurrently to the reaction solution formed in step b).

In yet another alternative, step d) may be conducted prior to step c), i.e., the seeding material, Form A of atazanavir sulfate, may be mixed with the reaction solution formed in step b) before the antisolvent is mixed with the reaction solution.

Preferably, the process as described above further comprises a step of mixing an additional amount of antisolvent with the seeded mixture after the seeding step. The antisolvent may be one or more of the antisolvents discussed above. In other words, after conducting the above discussed steps a)-d), an additional amount of antisolvent may be mixed with the seeded mixture after the seeding step d) but prior to the isolating step e).

Preferably, the process as described above further comprises a step of cooling the seeded mixture to a temperature of 0-25° C. for a period of 1-24 hr to facilitate formation of Form A.

Preferably, step a) is conducted at a temperature of 20-50° C., more preferably, 20-30° C.

The solvent discussed above is preferably ethanol.

The anti-solvent is preferably methyl tert-butyl ether.

The sulfuric acid discussed above is aqueous or concentrate, preferably concentrate.

The isolating step e) may comprise steps of stirring the seeded mixture to facilitate formation of Form A, filtering, washing, and drying to obtain Form A in solid form. The step of drying is preferably conducted under vacuum at 40-50° C. for about 16 hr.

In compassion with the process reported by others, Form A obtained in accordance with the process of the present invention is substantially free of any residual solvent impurities and potential genotoxic impurity (PGI), such as mesityl oxide (4-methyl-3-penten-2-one).

Other objects and features of the present invention will become apparent from the following detailed description.

DETAILED DESCRIPTION OF THE PRESENTLY PREFERRED EMBODIMENTS

The following preferred embodiments are provided to further illustrate, but not to limit the present invention.

As used herein, Form A of atazanavir sulfate is as defined in U.S. Pat. No. 7,829,720, which is herein incorporated by reference. For example, Form A crystals may be characterized by unit cell parameters substantially equal to the following:

Cell Dimensions:
a=9.86(5) Å
b=29.45(6) Å
c=8.327(2) Å
α=93.56(2)°
β=11.477(3)°
γ=80.49(3)°

EXAMPLE 1

3.12 mL of sulfuric acid (5 M, 1.1 equiv) was added into the mixture of 10 g of atazanavir base and 80 mL of IPA (8 vol) at 20-30° C. 60 mL of IPAc (6 vol.) was added into the resulting clear amber solution at 20-30° C. 70 mg of Atazanavir sulfate in Form A (0.7% wt) was added, and the mixture was stirred at 20-30° C. for 1 hr. 60 mL of IPAc (6 vol.) was added into the slurry and then stirred at 20-30° C. for 4 hr. The product was filtered, washed with a mixture of IPA/IPAc (1:1, 20 mL, 2 vol), and dried under vacuum at 40-50° C. for 16 hr to afford atazanavir sulfate in Form A (85% yield, >99.8% HPLC purity).

EXAMPLE 2

0.85 mL of sulfuric acid (concentrate, 1.1 equiv) was added into the mixture of 10 g of atazanavir base and 60 mL of EtOH (200 proof, 6 vol) at 20-30° C. 60 mL of MTBE (6 vol) was added into the resulting clear amber solution at 20-30° C. 70 mg of Atazanavir sulfate in Form A (0.7% wt) was added, and the mixture was stirred at 20-30° C. for 1 hr. 60 mL of MTBE (6 vol) was added into the slurry and then stirred at 20-30° C. for 1 hr then 0-5° C. for 2 hr The product was filtered, washed with a mixture of EtOH/MTBE (1:4, 20 mL, 2 vol), and dried under vacuum at 40-50° C. for 16 hr to afford atazanavir sulfate in Form A (9.09 g, 87% yield, >99.9% HPLC purity).

EXAMPLE 3

0.085 mL of sulfuric acid (concentrate, 1.1 equiv) was added into the mixture of 1 g of atazanavir base, 7.5 mL of EtOH (7.5 vol) and 7.5 mL of MTBE (7.5 vol) at 20-30° C. The resulting clear amber solution was stirred at 20-30° C. for 4 hr. The product was filtered, washed with a mixture of EtOH/MTBE (1:2, 3 mL, 3 vol), and dried under vacuum at 40-50° C. for 16 hr to afford atazanavir sulfate in Form A (1.04 g, 91% yield, 99.9% HPLC purity).

EXAMPLE 4

14.2 mL of sulfuric acid (5 M, 1.0 equiv) was added into the solution of 50 g of atazanavir base and 350 mL of IPA (7 vol) at 40-50° C. After the resulting amber solution was clear, it was filtered and washed with 50 mL of IPA (1 vol). 40 mL of IPAc (4 vol.) and atazanavir sulfate in Form A (0.7% wt) was added into the resulting clear amber solution at 40-50° C. and then stirred at 40-50° C. for 1 hr. The resulting slurry was cooled to 20-30° C. 80 mL of IPAc (8 vol) was added into the solution and then stirred at 20-30° C. for 4 hr. The product was filtered, washed with a mixture of IPA/IPAc (1:1, 100 mL, 2 vol), and dried under vacuum at 40-50° C. for 16 hr to afford atazanavir sulfate in Form A (86% yield, >99.9% HPLC purity).

EXAMPLE 5

10 g of atazanavir base was dissolved in 12 mL of N-methylpyrrolidone (NMP, 1.2 vol) and 100 mL of IPA (10 vol) and then warmed to 80-90° C. for dissolution. The clear solution was cooled to 70-75° C. followed by filtration while maintaining 65-75° C., and then washed with IPA (10 mL, 1 vol). The filtrate collected was cooled to 60° C., and then 0.74 mL of sulfuric acid (concentrated, 1.0 equiv) and 60 mL of IPAc (6 vol) were added at 50-60° C. 0.7 g of atazanavir sulfate in Form A (0.7% wt) was added then stirred at 50-60° C. for 1 hr then cooling to 20-30° C. 60 mL of IPAc (6 vol) was added into the solution and the mixture was stirred at 20-30° C. for 4 hr. The product was filtered, washed with a mixture of IPA/IPAc (2:1, 20 mL, 2 vol), and dried under vacuum at 40-50° C. for 16 hr to afford atazanavir sulfate in Form A (68% yield, >99.9% HPLC purity).

The invention is not limited by the embodiments described above which are presented as examples only but can be modified in various ways within the scope of protection defined by the appended patent claims.

EXAMPLE 6

To a 500 mL round-bottomed flask equipped with a magnetic stir was charged atazanavir base (19.0 g) and IPA (114 mL, 6 vol) followed by 5M sulfuric acid (5.32 mL, 1.0 equiv) at 20-30° C. The resulting clear amber solution was added EtOAc (114 mL, 6 vol) at 20-30° C. Atazanavir sulfate in Form A (0.25% wt) was added, and the mixture was stirred at 20-30° C. for 4 hr. The product was filtered, washed with a mixture of IPA/EA (1:1, 40 mL, 2 vol), and dried vacuum at 40-50° C. for 16 hr to afford atazanavir sulfate in Form A (17 g, 78% yield, 99.9% HPLC purity).

EXAMPLE 7

To a 200 mL round-bottomed flask equipped with a magnetic stir was charged atazanavir base (10.0 g) and 200 proof EtOH (75 mL, 7.5 vol) followed by concentrated sulfuric acid (0.85 mL, 1.1 equiv) at 20-30° C. The resulting clear amber solution was added MTBE (75 mL, 7.5 vol) at 20-30° C. Atazanavir sulfate in Form A (0.25% wt) was added, and the mixture was stirred at 20-30° C. for 4 hr. The product was filtered, washed with a mixture of EtOH/MTBE (1:1, 20 mL, 2 vol), and dried under vacuum at 40-50° C. for 16 hr to afford atazanavir sulfate in Form A (9.09 g, 79% yield, >99.9% HPLC purity).

EXAMPLE 8

To a 20 mL sample vial equipped with a magnetic stir was charged atazanavir base (1.0 g) and a mixture of 99.5% EtOH/ EtOAc (1/1, 7.5 mL, 7.5 vol) followed by concentrated sulfuric acid (0.085 mL, 1.1 equiv) at 20-30° C. The resulting clear amber solution was stirred at 20-30° C. for 4 hr. The product was filtered, washed with a mixture of EtOH/EA (1:1, 2 mL, 2 vol), and dried under vacuum at 40-50° C. for 16 hr to afford atazanavir sulfate in Form A (0.61 g, 55% yield, 99.9% HPLC purity).

EXAMPLE 9

To a 250 mL round-bottomed flask equipped with a magnetic stir was charged atazanavir base (5.0 g) and 99.5% EtOH (30 mL, 6 vol) followed by concentrated sulfuric acid (0.425 mL, 1.1 equiv) at 20-30° C. The resulting clear amber solution was added EtOAc (60 mL, 12 vol) at 20-30° C. Atazanavir sulfate in Form A (0.25% wt) was added, and the mixture was stirred at 20-30° C. for 4 hr. The product was filtered, washed with a mixture of EtOH/EA (1:2, 15 mL, 3 vol), and dried under vacuum at 40-50° C. for 16 hr to afford atazanavir sulfate in Form A (3.8 g, 66% yield, 99.9% HPLC purity).

EXAMPLE 10

To a 20 mL sample viral equipped with a magnetic stir was charged atazanavir base (1.0 g), 99.5% EtOH (mL, 1 vol), and MeCN (4 mL, 4 vol) at 20-30° C. Concentrated sulfuric acid (0.085 mL, 1.1 equiv) was added at 20-30° C., and the resulting clear amber solution was stirred at 20-30° C. for 4 hr. The product was filtered, washed with a mixture of EtOH/MeCN (1:4, 5 mL, 5 vol), and dried under vacuum at 40-50° C. for 16 hr to afford atazanavir sulfate in Form A (0.47 g, 42% yield, 99.9% HPLC purity).

EXAMPLE 11

To a 250 mL round-bottomed flask equipped with a magnetic stir was charged atazanavir base (5.0 g) and 99.5% EtOH (40 mL, 8 vol) followed by concentrated sulfuric acid (0.425 mL, 1.1 equiv) at 20-30° C. The resulting clear amber solution was added Cyclohexane (20 mL, 4 vol) at 20-30° C. Atazanavir sulfate in Form A (0.7% wt) was added, and the mixture was stirred at 20-30° C. for 1 hr. More cyclohexane (20 mL, 4 vol) was added at 20-30° C., and the slurry was stirred at 20-30° C. for 1 hr and cooled to 0-5° C. for 2 hr. The product was filtered, washed with a mixture of EtOH/cyclohexane (1:4, 10 mL, 2 vol), and dried under vacuum at 40-50° C. for 16 hr to afford atazanavir sulfate in Form A (4.7 g, 85% yield, 99.8% HPLC purity).

We claim:

1. A process of making Form A of atazanavir sulfate comprising:
    a) mixing atazanavir free base with a solvent selected from the group consisting of methanol (MeOH), ethanol (EtOH), isopropanol (IPA), N-methylprrolidone (NMP) and combinations thereof;
    b) reacting sulfuric acid with the atazanavir free base in the mixture formed in step a) to form a reaction solution comprising atazanavir sulfate;
    c) mixing an antisolvent with the reaction solution;
    d) seeding the mixture formed in step c) with an effective amount of Form A of atazanavir sulfate to form a seeded mixture comprising Form A of atazanavir sulfate; and
    e) isolating Form A of atazanavir sulfate in solid form from the seeded mixture;
    wherein the antisolvent is selected from the group consisting of methyl tert-butyl ether (MTBE), ethyl acetate (EtOAc), acetonitrile (MeCN), isopropyl acetate (IPAc), cyclohexane, and combinations thereof.

2. The process of claim 1 further comprising a step of mixing an additional amount of an antisolvent with the seeded mixture prior to the isolating step, wherein the antisolvent is selected from the group consisting of methyl tert-butyl ether (MTBE), ethyl acetate (EtOAc), acetonitrile (MeCN), isopropyl acetate (IPAc), cyclohexane, and combinations thereof.

3. The process of claim 1, further comprising a step of cooling the seeded mixture to a temperature of 0-25° C. for a period of 1-24 hr to facilitate formation of Form A of atazanavir sulfate.

4. The process of claim 1 wherein step a) is conducted at a temperature of 20-50° C.

5. The process of claim 4 wherein step a) is conducted at a temperature of 20-30° C.

6. The process of claim 1 wherein the solvent is ethanol.

7. The process of claim 1 wherein the anti-solvent is methyl tert-butyl ether.

8. The process of claim 1 wherein the sulfuric acid is aqueous or concentrate.

9. The process of claim 8 wherein the sulfuric acid is concentrate.

10. The process of claim 1 wherein the step of isolating comprises steps of stirring the seeded mixture to facilitate formation of Form A of atazanavir sulfate, filtering, washing, and drying to obtain Form A of atazanavir sulfate in solid form.

11. The process of claim 10 wherein the drying is conducted under vacuum at 40-50° C. for about 16 hr.

12. A process of making Form A of atazanavir sulfate comprising:
    a') mixing atazanavir free base with a solvent selected from the group consisting of methanol (MeOH), ethanol (EtOH), isopropanol (IPA), N-methylprrolidone (NMP) and combinations thereof;
    b') mixing an antisolvent with the mixture formed in step a');
    c') reacting sulfuric acid with the atazanavir free base in the mixture formed in step b) to form a reaction solution comprising atazanavir sulfate;
    d') seeding the reaction solution formed in step c') with an effective amount of Form A of atazanavir sulfate to form a seeded mixture comprising Form A of atazanavir sulfate; and
    e') isolating Form A of atazanavir sulfate in solid form from the seeded mixture;
    wherein the antisolvent is selected from the group consisting of methyl tert-butyl ether (MTBE), ethyl acetate (EtOAc), acetonitrile (MeCN), isopropyl acetate (IPAc), cyclohexane, and combinations thereof.

13. A process of making Form A of atazanavir sulfate comprising:
    a") mixing atazanavir free base with a solvent selected from the group consisting of methanol (MeOH), ethanol (EtOH), isopropanol (IPA), N-methylprrolidone (NMP) and combinations thereof;
    b") reacting sulfuric acid with the atazanavir free base in the mixture formed in step a") to form a reaction solution comprising atazanavir sulfate;
    c") mixing an effective amount of Form A of atazanavir sulfate as seeding crystals and an antisolvent with the reaction solution to form a seeded mixture comprising Form A of atazanavir sulfate; and
    d") isolating Form A of atazanavir sulfate in solid form from the mixture formed in step d");
    wherein the antisolvent is selected from the group consisting of methyl tert-butyl ether (MTBE), ethyl acetate (EtOAc), acetonitrile (MeCN), isopropyl acetate (IPAc), cyclohexane, and combinations thereof.

14. The process of claim 13 wherein in step c", the seeding crystals are mixed with the reaction solution before the antisolvent is mixed with the reaction solution.

15. The process of claim 13 wherein in step c", the seeding crystals and the antisolvent are mixed with the reaction solution concurrently.

\* \* \* \* \*